(12) United States Patent
Venkatesan

(10) Patent No.: US 11,318,030 B1
(45) Date of Patent: May 3, 2022

(54) STENT ASSEMBLY FOR USE IN TREATING BIFURCATION LESIONS AND METHODS OF MAKING AND USING THE SAME

(71) Applicant: Archana Venkatesan, Suffolk, VA (US)

(72) Inventor: Archana Venkatesan, Suffolk, VA (US)

(*) Notice: Subject to any disclaimer, the term of this patent is extended or adjusted under 35 U.S.C. 154(b) by 213 days.

(21) Appl. No.: 16/541,101

(22) Filed: Aug. 14, 2019

Related U.S. Application Data

(60) Provisional application No. 62/720,145, filed on Aug. 21, 2018, provisional application No. 62/718,405, filed on Aug. 14, 2018.

(51) Int. Cl.
| | |
|---|---|
| *A61F 2/954* | (2013.01) |
| *A61F 2/958* | (2013.01) |
| *A61F 2/856* | (2013.01) |
| *A61L 31/06* | (2006.01) |
| *A61B 34/20* | (2016.01) |
| *A61F 2/06* | (2013.01) |
| *A61F 2/95* | (2013.01) |

(52) U.S. Cl.
CPC .............. *A61F 2/954* (2013.01); *A61F 2/958* (2013.01); *A61L 31/06* (2013.01); *A61B 34/20* (2016.02); *A61F 2/856* (2013.01); *A61F 2/9522* (2020.05); *A61F 2002/067* (2013.01); *A61F 2250/0067* (2013.01)

(58) Field of Classification Search
CPC ........ A61F 2/954; A61F 2/958; A61F 2/9522; A61F 2/856; A61F 2002/067; A61F 2250/0067; A61F 2002/065; A61F 2/06; A61F 2/07; A61F 2002/077; A61F 2/04; A61F 2002/075; A61F 2002/826; A61F 2002/828; A61L 31/06; A61B 34/20
See application file for complete search history.

(56) References Cited

U.S. PATENT DOCUMENTS

| | | | | |
|---|---|---|---|---|
| 2005/0245941 | A1* | 11/2005 | Vardi | A61F 2/954 606/108 |
| 2006/0173528 | A1* | 8/2006 | Feld | A61F 2/91 623/1.15 |
| 2007/0061003 | A1* | 3/2007 | Shmulewitz | A61F 2/91 623/1.16 |
| 2010/0324664 | A1* | 12/2010 | Holzer | A61F 2/90 623/1.35 |
| 2013/0268047 | A1* | 10/2013 | Bourang | A61F 2/852 623/1.11 |

\* cited by examiner

*Primary Examiner* — Tan-Uyen T Ho
*Assistant Examiner* — Bridget E. Rabaglia
(74) *Attorney, Agent, or Firm* — NK Patent Law

(57) ABSTRACT

The presently disclosed subject matter is directed to a dual stent assembly useful in treating one or more bifurcation lesions in a subject. The dual stent assembly includes a first stent and a second stent. The first stent comprises a body, proximal and distal ends, and a flare positioned at the proximal end. The first stent translates between a compressed configuration and a deployed configuration. The second stent is defined by a body comprising a sidewall, proximal and distal ends, and an orifice positioned on the body that extends through the sidewall. The second stent is translatable between a compressed configuration and a deployed configuration. The orifice is sized and shaped to align with the proximal end of the first stent when the second stent is deployed.

11 Claims, 12 Drawing Sheets

STENT ASSEMBLY FOR USE IN TREATING BIFURCATION LESIONS AND METHODS OF MAKING AND USING THE SAME

CROSS-REFERENCE TO RELATED APPLICATIONS

This application claims priority to U.S. Provisional Patent Application No. 62/720,145, filed on Aug. 21, 2018, and also claims priority to U.S. Provisional Patent Application No. 62/718,405, filed on Aug. 14, 2018, the entire contents of which are all hereby incorporated herein by reference.

TECHNICAL FIELD

The presently disclosed subject matter relates to a stent assembly for use in treating bifurcation lesions (e.g., through percutaneous coronary intervention), and to methods of making and using the disclosed stent assembly. It should be appreciated that the disclosed stent assembly is not limited and can be used for a wide variety of purposes.

BACKGROUND

Heart disease, specifically coronary artery disease, is a major cause of death, disability, and healthcare expense in the United States, other industrialized countries, and developing nations (and other nations). A number of methods and devices for treating heart disease have been developed, some of which are specifically designed to treat the complications resulting from atherosclerosis and other forms of coronary arterial narrowing. For example, percutaneous coronary intervention (PCI) is a therapeutic method that physically expands the lumens of narrowed coronary arteries. PCI involves delivering a treatment device to the affected area of a blood vessel to open the blocked site. Angioplasty procedures are commonly performed wherein a balloon catheter is tracked through the vasculature to the constriction and then expanded to open the blockage. A stent can further be deployed at the site to help maintain the patency of the vessel. However, lesions occurring at or near a bifurcation of the blood vessel (e.g., the intersection of a main vessel with a side branch vessel) are challenging to treat due to their morphological heterogeneity, high restenosis rate, and the long-term risk of occurrence of major adverse cardiac events. It would therefore be beneficial to provide an improved system and method for use in treating bifurcation lesions.

SUMMARY

The presently disclosed subject matter is generally directed to methods of deploying a dual stent assembly at a lesion site located at a bifurcation in a vessel defined by a main branch and a side branch. In some embodiments, a method comprises positioning a side branch stent in the side branch of the bifurcation site, wherein the side branch stent comprises a body and a proximal flare configured at a proximal end, and wherein the side branch stent is positioned such that the proximal end is aligned with an ostium of the vessel. The method also includes simultaneously deploying the side branch stent in close approximation to a side branch vessel wall and crimping the proximal end of the side branch sten. The method further includes positioning a main branch stent in the main branch of the bifurcation site, wherein the main branch stent comprises a main body with a longitudinal axis and a central orifice in a central portion of the longitudinal axis. The dual stent assembly as such is deployed at a lesion site located at the bifurcation site and the central orifice is aligned with the proximal flare of the side branch stent. In other embodiments, a method comprises predilating the side branch and main branch of the vessel by positioning a main branch balloon catheter in the main branch and a side branch balloon catheter in the side branch of the bifurcation, and then dilating the balloon catheters using an inflation device. The method further comprises deflating the balloon catheters and retracting them from the bifurcation site, and positioning a side branch stent in the side branch of the bifurcation site. The side branch stent comprises a body and a flare configured at a proximal end. The side branch stent is positioned such that the proximal end is aligned with an ostium of the vessel. The method includes positioning the main branch balloon catheter in the main branch of the bifurcation site, and simultaneously deploying the side branch stent in close approximation to the side branch vessel wall at a first pressure and inflating the main branch balloon catheter at a second pressure. The first pressure is greater than the second pressure, whereby the proximal flare is opened. The method comprises deflating the side branch stent balloon and the main branch balloon catheter balloon, crimping the proximal end of the side branch stent by inflating the balloon of the main branch balloon catheter to a pressure that is greater than the second pressure, deflating and retracting the main branch balloon catheter, retracting the side branch guide wire to a proximal portion of the main branch, and positioning a main branch stent in the main branch of the bifurcation. The main branch stent comprises a main body with a longitudinal axis and a central orifice in a central portion of the longitudinal axis. The central orifice is aligned with the proximal flare of the side branch stent. The method includes inflating the balloon of the main branch stent catheter to a pressure greater than the second pressure, removing the main branch stent balloon, rewiring the side branch using a guide wire, positioning a main branch balloon catheter in the main branch of the bifurcation and a side branch balloon catheter in the side branch of the bifurcation, performing simultaneous kissing inflation of the main branch balloon catheter and the side branch balloon catheter, and simultaneously deflating and retracting the main branch balloon catheter and the side branch balloon catheters. The dual stent assembly is deployed at a lesion site located at the bifurcation.

In some embodiments, the main branch stent, side branch stent, or both are constructed from one or more biocompatible materials. The one or more biocompatible materials can include a metal selected from stainless steel, nitinol, cobalt, cobalt-based alloy, gold, tantalum, platinum, platinum iridium, niobium, tungsten, nickel, titanium, stainless steel/titanium composite, chromium, cobalt/chromium alloys, magnesium, aluminum, or combinations thereof. In some embodiments, the one or more biocompatible materials include a polymeric material selected from cellulose acetate, cellulose nitrate, silicone, polyethylene terephthalate, polyurethane, polyamide, polyester, polyorthoester, polyanhydride, polyether sulfone, polycarbonate, polypropylene, ultra-high molecular weight polyethylene, polytetrafluoroethylene, polylactic acid, polyglycolic acid, polyanhydride, polycaprolactone, polyhydroxybutyrate valerate, or combinations thereof.

In some embodiments, the orifice is configured in a round, hexagonal, octagonal, or oval shape. In some embodiments, the orifice has a diameter of about 2 to 20 mm.

In some embodiments, the main branch stent, side branch stent, or both comprise one or more radiopaque materials selected from bismuth (and salts thereof), barium (and salts thereof), tantalum, tungsten, halfnium, gold, platinum, molybdenum, zirconium oxide, titanium, and combinations thereof.

In some embodiments, the main branch stent, side branch stent, or both comprises one or more therapeutic agents selected from antineoplastic agents, antiproliferative agents, antibiotics, antithrombogenic agents, anticoagulants, anti-platelet agents, anti-inflammatory agents, or combinations thereof.

In some embodiments, the method further comprises performing an angiogram to confirm proper positioning of the main branch stent, side branch stent, or both.

In some embodiments, the vessel is a coronary vessel.

In some embodiments, the presently disclosed subject matter is directed to a dual stent assembly comprising a first stent defined by a body, proximal and distal ends, and a flare positioned at the proximal end, wherein the first stent translates between a compressed configuration and a deployed configuration. The stent assembly further includes a second stent defined by a body comprising a sidewall, proximal and distal ends, and an orifice positioned on the body that extends through the sidewall. The second stent is translatable between a compressed configuration and a deployed configuration, and the orifice is sized and shaped to align with the proximal end of the first stent when the second stent is deployed.

In some embodiments, the first stent, second stent, or both are constructed from one or more biocompatible materials. The one or more biocompatible materials can include a metal selected from stainless steel, nitinol, cobalt, cobalt-based alloy, gold, tantalum, platinum, platinum iridium, niobium, tungsten, nickel, titanium, stainless steel/titanium composite, chromium, cobalt/chromium alloys, magnesium, aluminum, or combinations thereof. In some embodiments, the one or more biocompatible materials include a polymeric material selected from cellulose acetate, cellulose nitrate, silicone, polyethylene terephthalate, polyurethane, polyamide, polyester, polyorthoester, polyanhydride, polyether sulfone, polycarbonate, polypropylene, ultra-high molecular weight polyethylene, polytetrafluoroethylene, polylactic acid, polyglycolic acid, polyanhydride, polycaprolactone, polyhydroxybutyrate valerate, or combinations thereof.

In some embodiments, the first stent and the second stent are configured to be deployed at a lesion site located at a bifurcation in a vessel defined by a main branch and a side branch. In some embodiments, the first stent is configured to be positioned in the side branch of the vessel at the bifurcation. The proximal flare of the first stent can be configured to be positioned adjacent to the ostium of the vessel. The second stent can be configured to be positioned in the main branch of the vessel at the bifurcation. In some embodiments, the second stent is configured such that the orifice is positioned adjacent to or at the proximal flare of the first stent.

In some embodiments, the vessel is a coronary vessel.

BRIEF DESCRIPTION OF THE DRAWINGS

The foregoing summary, as well as the following detailed description of preferred embodiments, is better understood when read in conjunction with the appended drawings. For the purposes of illustration, there is shown in the drawings exemplary embodiments; however, the presently disclosed invention is not limited to the specific methods and instrumentalities disclosed.

In the drawings.

DETAILED DESCRIPTION

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used, representative methods, devices, and materials are now described.

Following long-standing patent law convention, the terms "a", "an", and "the" refer to "one or more" when used in the subject specification, including the claims. Thus, for example, reference to "a stent" can include a plurality of such stents, and so forth.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed packages and methods.

Figure 1A:
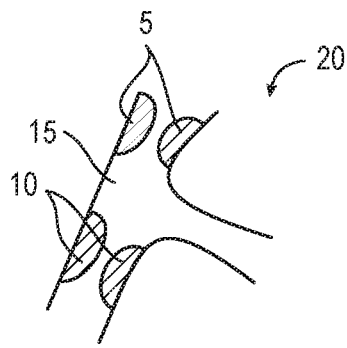
FIG. 1A is a schematic diagram illustrating a blood vessel with a plurality of proximal and distal lesions in the main branch of the vessel in accordance with embodiments of the present disclosure.
Figure 1B:
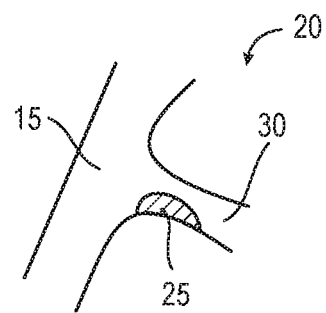
FIG. 1B is a schematic diagram illustrating a blood vessel comprising a lesion positioned within a side branch in accordance with embodiments of the present disclosure.
Figure 1C:
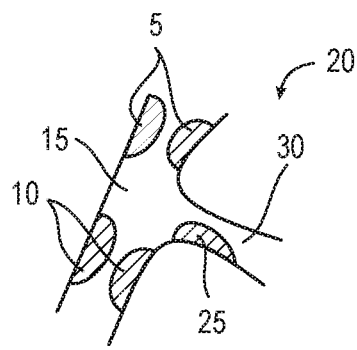
FIG. 1C is a schematic diagram illustrating a blood vessel branch point with both main branch and side branch lesions in accordance with embodiments of the present disclosure. It should be noted that for FIGS. 1A-1C, the configuration, thickness, and/or number of struts are not exactly shown and can be (but are not limited to) open, closed, etc.

The presently disclosed subject matter is directed to a dual stent technique that is particularly useful in treating one or more bifurcation lesions in a subject. The term "bifurcation lesion" refers to a narrowing in a parent vessel and/or side branch vessel due to (but not limited to) atherosclerosis or other causes at or adjacent to the branch point. FIG. 1A illustrates one embodiment of a coronary artery branch point in which stenosis occurs as a plurality of proximal and distal lesions 5, 10 in main branch 15 of vessel 20. FIG. 1B illustrates vessel 20 comprising side branch lesion 25 positioned within side branch 30 at a coronary artery branch point. In some embodiments, both main branch 15 and side branch 30 of vessel 20 can include one or more lesions, as shown in FIG. 1C. It should be appreciated that the disclosed stent and technique can be used with a variety of lesions, such as (but not limited to) ostial alone, promixo ostial, and the like.

Figure 2A:
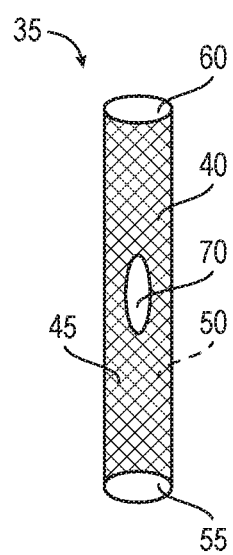
FIG. 2A is a perspective view of a main branch stent in a compressed configuration in accordance with embodiments of the present disclosure.

Traditionally, lesions occurring at or near a bifurcation of a blood vessel (e.g., the intersection of main branch 15 with side branch 30) are challenging to treat due to their morphological heterogeneity and high restenosis rate. However, the presently disclosed dual stent assembly can be used to ameliorate the shortcomings of the prior art. Particularly, the dual stent assembly includes a proximally-flared stent at the ostium of the side branch of a vessel, and a main branch stent with a central aperture aligned with the crimped proximal struts of the side branch stent. The main branch and side branch stents are positioned within a vessel to prevent re-narrowing of the vessel. FIG. 2A illustrates one embodiment of balloon-expandable main branch stent 35 in a pre-delivery, restrained (e.g., compressed) state with a reduced diameter. Once properly positioned within main branch 15, stent 35 is deployed to a delivery (e.g., extended) configuration, as illustrated in the embodiment of FIG. 2B.

Main branch stent 35 comprises body 40 of generally tubular shape that includes outer surface 45 and inner surface 50. The outer surface of body 40 faces (i.e., is juxtaposed with) an inner wall surface of main branch 15 of the vessel during use. Stent inner surface 50 faces a stream of fluid (e.g., blood) flowing through the lumen. Body 40 further includes first and second ends 55, 60. Body 40 is constructed by laser cutting metal and/or alloy material.

The disclosed stent further comprises aperture 70 positioned along a length of body 45, between proximal and distal ends 55, 60. As described in detail below, main branch stent 35 is positioned in a blood vessel such that aperture 70 is located proximal to the vessel side branch (i.e., facing the opening of the side branch vessel). As shown in FIG. 2A, the aperture is free from any graft material or structural member to permit free, unobstructed flow of blood through the aperture. In some embodiments, the aperture can include a circumferential radiopaque ring and/or one or more radiopaque markers to provide an accurate landmark under fluoroscopy during placement.

Figure 2B:
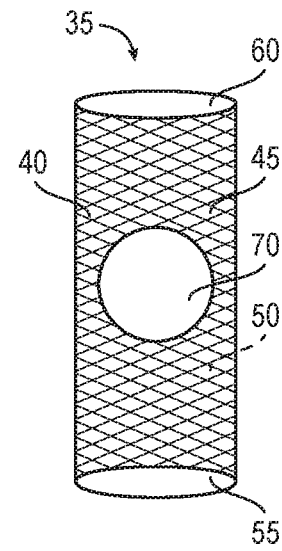
FIG. 2B is a perspective view of the main branch stent of FIG. 2A in a deployed configuration in accordance with embodiments of the present disclosure.

Aperture 70 can be configured in a rounded, hexagonal, octagonal, or oval shape when expanded, as shown in FIG. 2B. Further, the aperture can be configured with a diameter of about 2 to 20 mm, such as about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20 mm. However, the presently disclosed subject matter is not limited and the aperture can be configured in any desired shape or size suitable for a particular application.

Stent 35 can be formed from one or more biocompatible materials. The term "biocompatible" refers to a material that is compatible with the subject into which the material is implanted. For example, the stent can comprise one or more biocompatible metals and/or polymeric materials. Suitable biocompatible metals can include (but are not limited to) stainless steel, nitinol, MP35N®, cobalt, cobalt-based alloy (such as Elgiloy®), gold, tantalum, platinum, platinum iridium, niobium, tungsten, nickel, titanium, stainless steel/ titanium composite, chromium, cobalt/chromium alloys, magnesium, aluminum, or other biocompatible metals, composites, or alloys. Suitable biocompatible polymeric materials can include (but are not limited to) cellulose acetate, cellulose nitrate, silicone, polyethylene terephthalate, polyurethane, polyamide, polyester, polyorthoester, polyanhydride, polyether sulfone, polycarbonate, polypropylene, ultra-high molecular weight polyethylene, polytetrafluoroethylene, polylactic acid, polyglycolic acid, polyanhydride, polycaprolactone, polyhydroxybutyrate valerate, or mixtures or copolymers of these.

In some embodiments, body 40 can include one or more radiopaque materials to aid in visualization and/or adjustment of the stent during implantation, repositioning, or retrieval. Thus, stent 35 can be made selectively radiopaque at desired areas along wires 65 or can be constructed to be fully radiopaque, depending on the desired end-product and application. For example, stent 35 can include one or more radiopaque markers configured to provide fluoroscopic visualization for accurate deployment and positioning. Radiopaque markers can be affixed or incorporated (e.g., by welding, gluing, suturing, and the like) to the stent at a desired location. Alternatively, a radiopaque material can be added to stent 35 as a coating, using standard processes such as sputtering, plating, and/or co-drawing.

A wide variety of radiopaque materials and their salts and derivatives are suitable for use with the disclosed stent, including (but not limited to) bismuth (and salts thereof), barium (and salts thereof), tantalum, tungsten, halfnium, gold, platinum, molybdenum, zirconium oxide, titanium, and combinations thereof.

In some embodiments, stent 35 can include a therapeutic agent, such as (but not limited to) one or more antineoplastic agents, antiproliferative agents, antibiotics, antithrombogenic agents, anticoagulants, antiplatelet agents, anti-inflammatory agents, or combinations of the above. Such materials are well known in the art. The therapeutic agent can be applied using any known method, including (but not limited to) spraying, dipping, pouring, pumping, brushing, wiping, vacuum deposition, vapor deposition, plasma deposition, electrostatic deposition, ultrasonic deposition, epitaxial growth, electrochemical deposition, or any other method known.

Stent 35 is configured to be balloon-expandable. The term "balloon expandable" refers to a device that comprises a reduced profile configuration and an expanded profile configuration and undergoes a transition from the reduced configuration to the expanded configuration via the outward radial force of a balloon expanded by any suitable inflation medium.

Figure 3A:
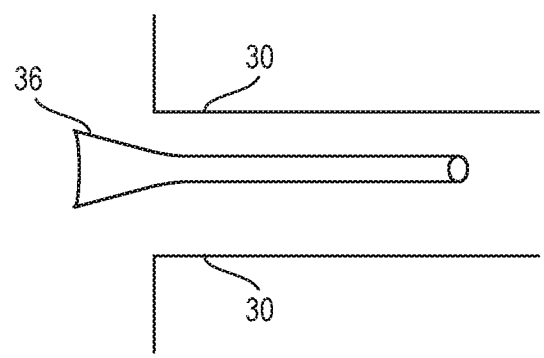
FIG. 3A is a front plan view of a side branch stent in a compressed configuration in accordance with embodiments of the present disclosure.
Figure 3B:
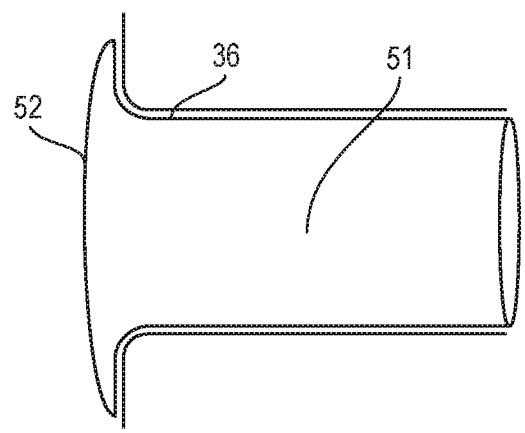
FIG. 3B is a perspective view of the side branch stent of FIG. 3B in a deployed configuration in accordance with embodiments of the present disclosure.

FIGS. 3A and 3B illustrate one embodiment of a side branch stent 36 comprising main body 51 and flare 52 configured at one end in compressed and expanded configurations, respectively.

Figure 4:
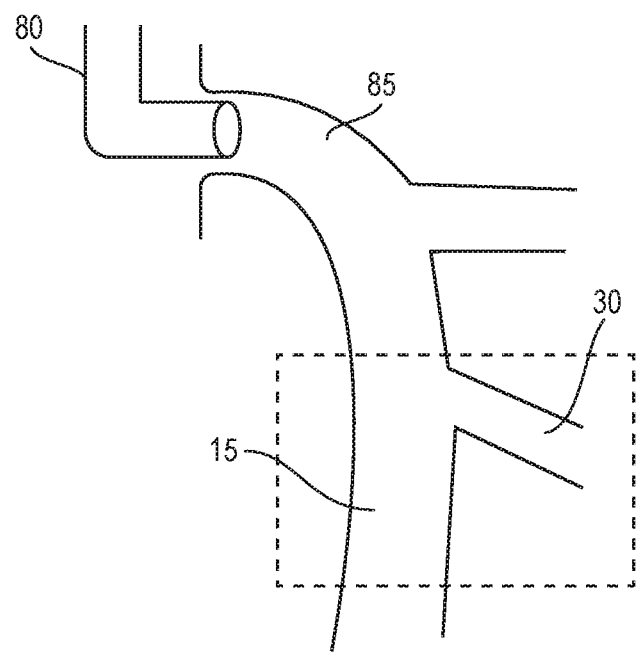
FIG. 4 is a schematic diagram illustrating a guide catheter being inserted into a blood vessel in accordance with embodiments of the present disclosure.
Figure 5:
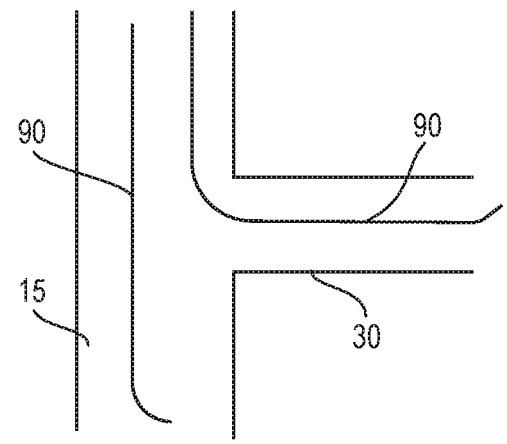
FIG. 5 is a schematic diagram illustrating guidewires positioned in the side branch and main branch of a blood vessel in accordance with embodiments of the present disclosure.

The following figures illustrate one embodiment of a method of percutaneous coronary intervention that includes the use of main branch stent 35 and side branch stent 36. As shown in FIG. 4, guide catheter 80 is advanced to coronary artery ostium 85. The guide catheter can be configured as an elongated tube to facilitate the implantation and/or delivery of a medical implement or device. Guide wires 90 are then advanced into side branch 30 and into main branch 15, as shown in FIG. 5.

Figure 6A:
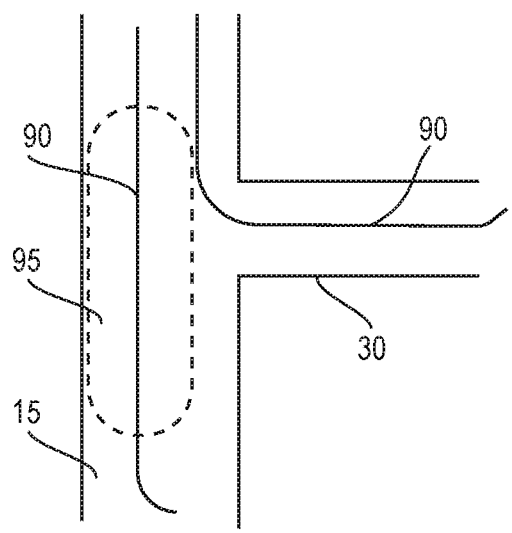
FIGS. 6A-6C are schematics illustrating three methods of pre-dilation in a blood vessel in accordance with embodiments of the present disclosure.
Figure 6B:
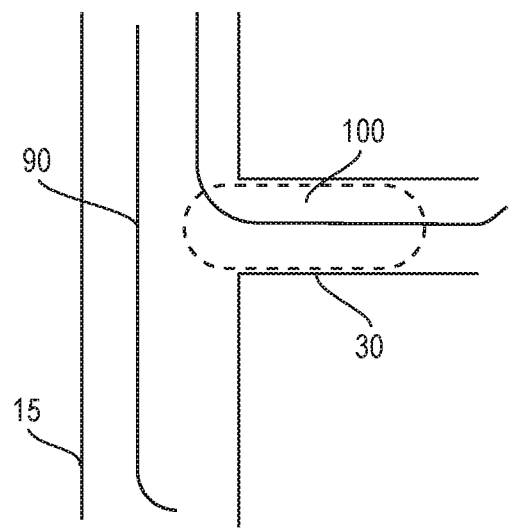
Figure 6C:
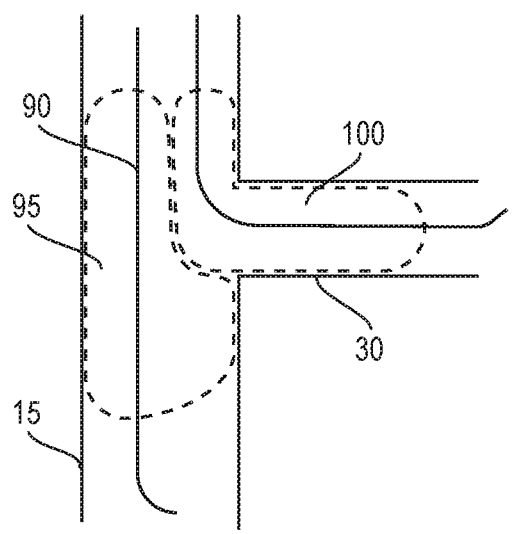

Pre-dilation for adequate site preparation is then performed using a balloon catheter. An appropriately-sized balloon is advanced over guidewires 90 in both the side branch and main branch. After angiographically confirming that the balloon positions in relation to the stenosis, dilation is performed using a balloon inflation device. Pre-dilation can be accomplished using three different methods. FIG. 6A illustrates one method of pre-dilation, where main branch balloon catheter 95 is inflated first, followed by inflation in side branch 30. FIG. 6B illustrates one method of pre-dilation where side branch balloon catheter 100 is inflated, followed by inflation of the main branch balloon catheter. FIG. 6C illustrates one embodiment of pre-dilation, showing simultaneous kissing balloon inflation of side branch balloon catheter 100 and main branch balloon catheter 95.

Figure 7:
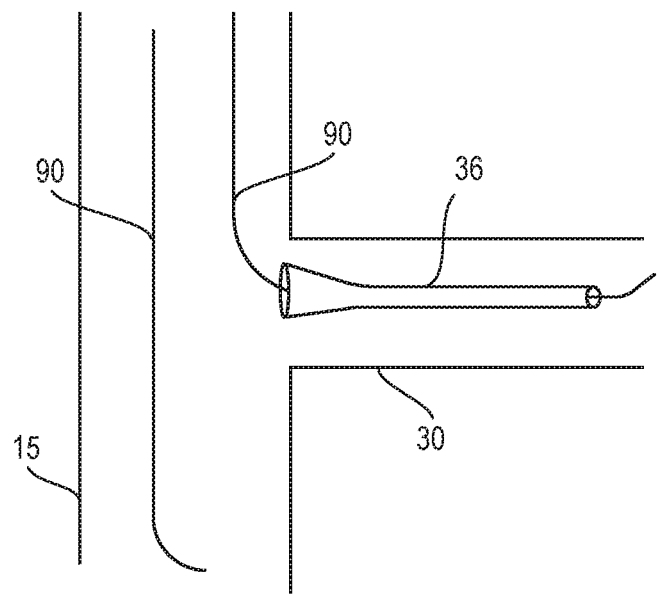
FIG. 7 is a schematic diagram illustrating appropriately sized side branch stent comprising a main body and flare configured at the proximal end advanced over the side branch wire into the side branch with its proximal end aligned to the ostium in accordance with embodiments of the present disclosure.

Following pre-dilation, the balloon catheter(s) are deflated and retracted over wire 90 and a follow up angiogram is performed to evaluate adequate site preparation. An appropriately sized side branch stent 36 (comprising a main body and a flare configured at the proximal end) is advanced of side branch wire 90 into the side branch with its proximal end aligned to the ostium, as shown in FIG. 7. The position of the stent can be confirmed through angiography.

Figure 8:
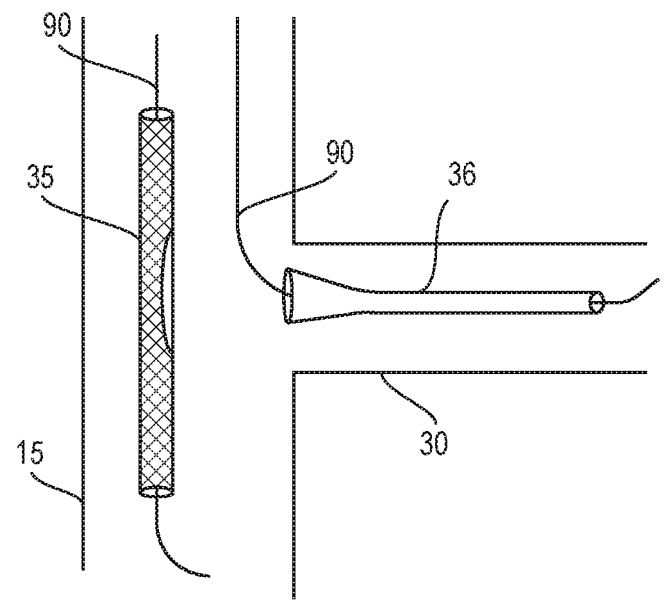
FIG. 8 is a schematic diagram illustrating a main branch balloon catheter positioned at the bifurcation site of a blood vessel in accordance with embodiments of the present disclosure.

The main branch balloon catheter is then advanced over the main branch wire 90 and positioned at the bifurcation site, as illustrated in FIG. 8.

Figure 9:
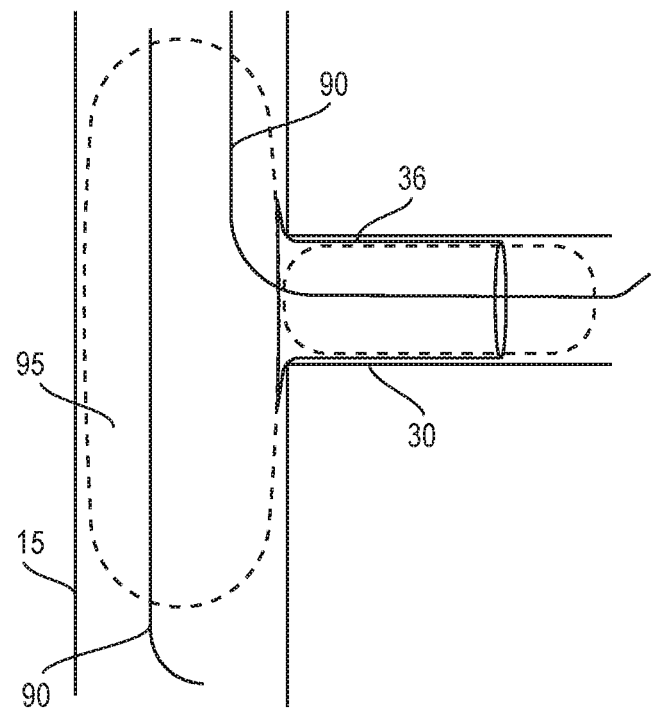
FIG. 9 is a schematic diagram illustrating low pressure inflation of a main branch balloon catheter and moderate to high pressure side branch balloon in a blood vessel in accordance with embodiments of the present disclosure.
Figure 10:
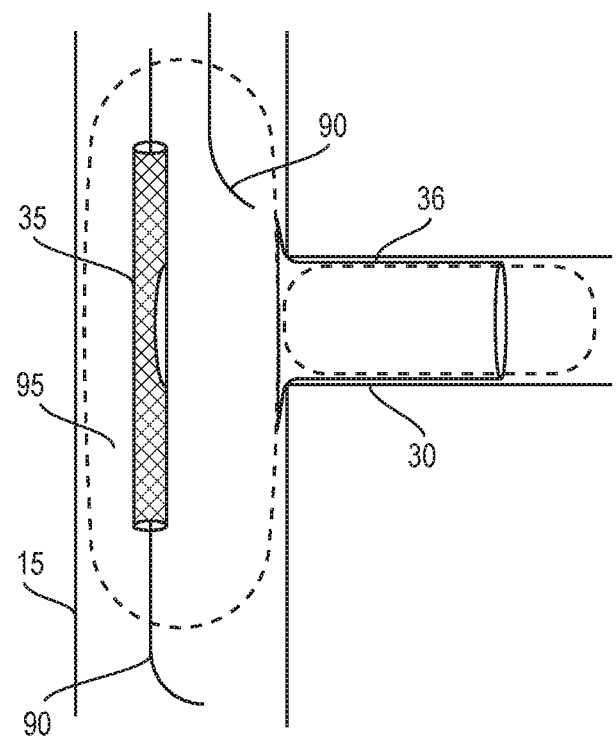
FIG. 10 is a schematic diagram illustrating high pressure inflation of a main branch catheter in a blood vessel in accordance with embodiments of the present disclosure.

Low pressure inflation of main branch balloon catheter 35 and moderate to high pressure inflation of side branch stent 36 are performed simultaneously, as shown in FIG. 9. In this way, the side branch stent is deployed with close approximation to the side branch vessel wall. The proximal flare of the side branch stent is also gently opened. The side branch stent balloon and the main branch balloon catheter are then deflated. The side branch stent balloon is retracted over wire 90. Following this step, high pressure inflation of the main branch balloon is performed to crimp the proximal end of the side branch stent to ensure close approximation with the ostium and the vessel wall, as shown in FIG. 10. This also helps to prevent plaque migration.

Figure 11:
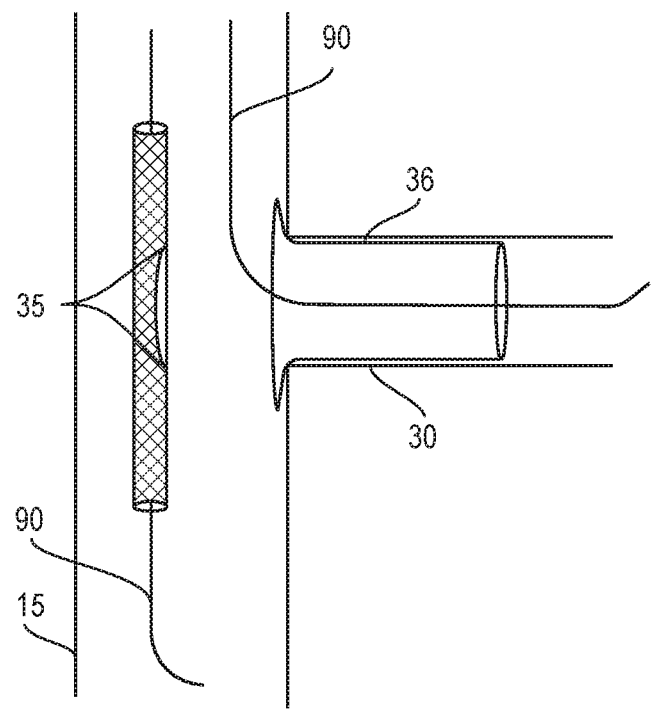
FIG. 11 is a schematic diagram illustrating placement of a main branch stent with central orifice in the middle of its longitudinal axis in the main branch following deflation and retraction of the main branch balloon catheter over the wire in the blood vessel. The orifice of the main branch stent is aligned with the proximal flared end of the side branch stent using radio opaque markers in accordance with embodiments of the present disclosure.

Main branch balloon catheter 95 is then deflated and retracted over wire 90. Main branch stent 35 with a central orifice in the middle of its longitudinal axis is then advanced over wire 90 and positioned in the main branch. The orifice of the main branch stent is aligned with the proximal flared end of side branch stent 36 using radio opaque markers, as shown in FIG. 11.

Figure 12:
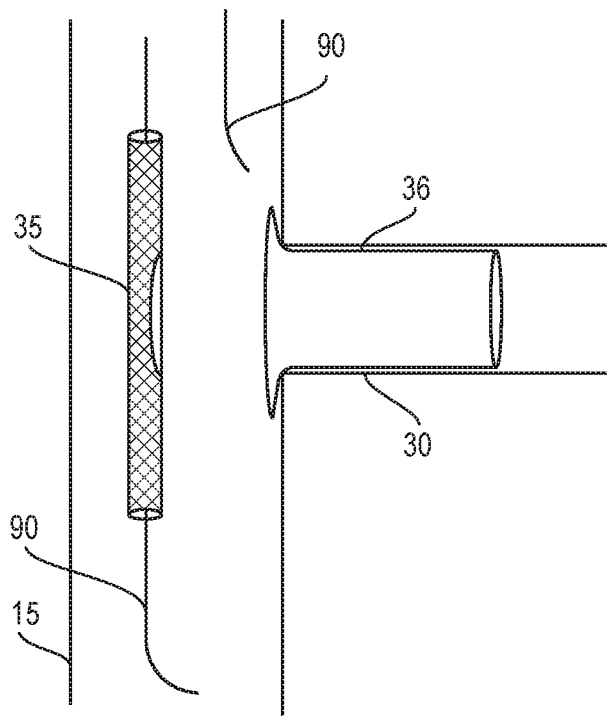
FIG. 12 is a schematic diagram illustrating a side branch guidewire retracted and positioned in a proximal portion of the main branch of a blood vessel in accordance with embodiments of the present disclosure.

Side branch guidewire 90 is then withdrawn and positioned in the proximal position of the main branch to provide clearance for the main branch stent catheter, as illustrated in FIG. 12.

Figure 13:
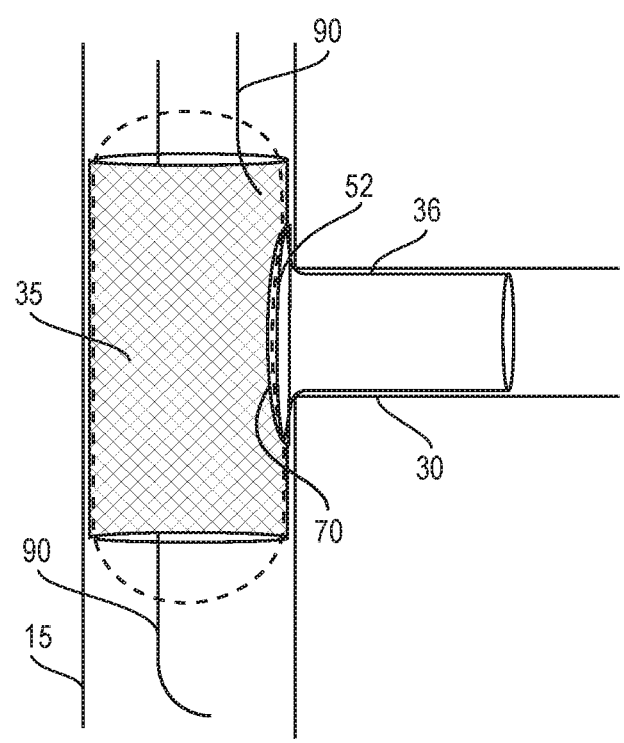
FIG. 13 is a schematic diagram illustrating inflation of a main branch stent balloon and deployment of the main branch stent in the main branch in a blood vessel in accordance with embodiments of the present disclosure.

The main branch stent balloon is inflated and the main branch stent is deployed at moderate to high pressure, as shown in FIG. 13.

Figure 14:
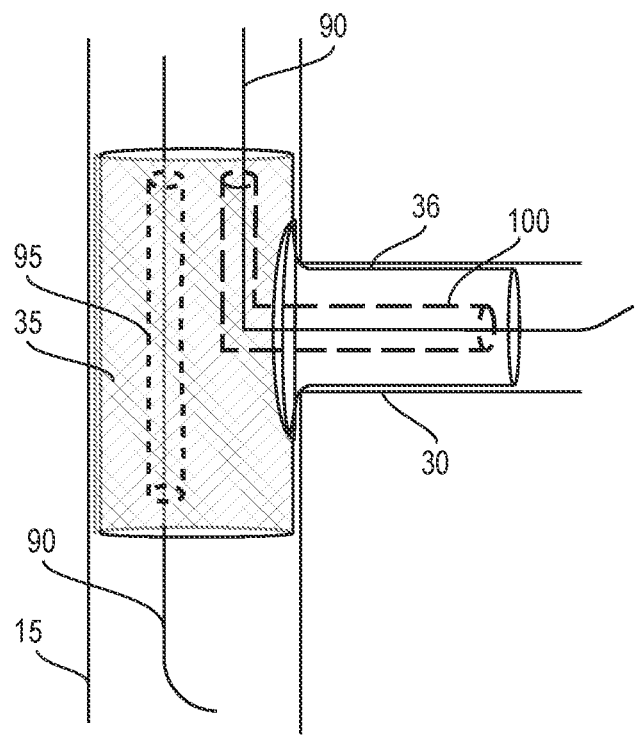
FIG. 14 is a schematic diagram illustrating rewired side branch using side branch guidewire following deflation and retraction over the wire of the main branch stent balloon. Also shown are balloon catheters positioned in the main branch and side branch in accordance with embodiments of the present disclosure.
Figure 15:
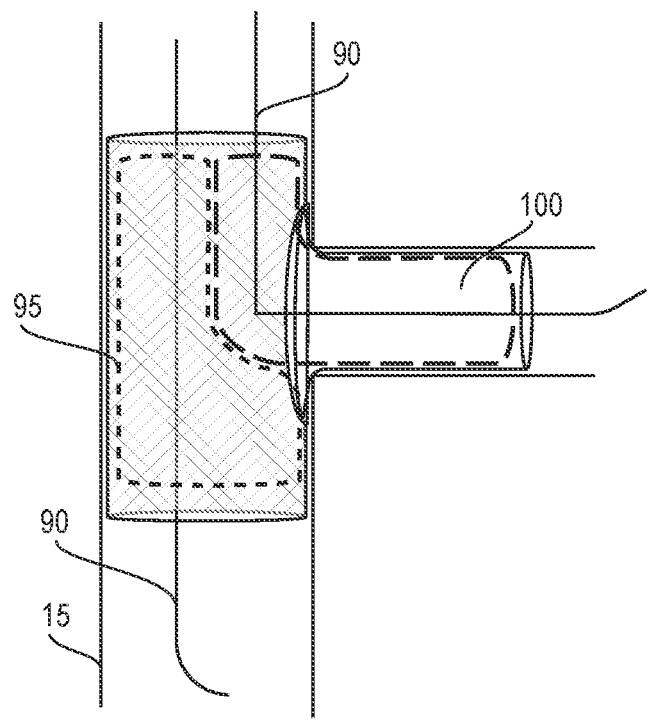
FIG. 15 is a schematic diagram illustrating kissing inflation in a main branch and side branch of a blood vessel in accordance in accordance with embodiments of the present disclosure.

As illustrated in FIG. 14, the side branch is rewired and the balloon catheters are positioned in the main branch and side branch. The side branch is rewired using the side branch guidewire. Appropriately-sized balloon catheters 95 and 100 are advanced over the main branch and side branch wires. The balloons are positioned at the main branch and side branch and simultaneous kissing inflation is performed, as shown in FIG. 15.

Figure 16:
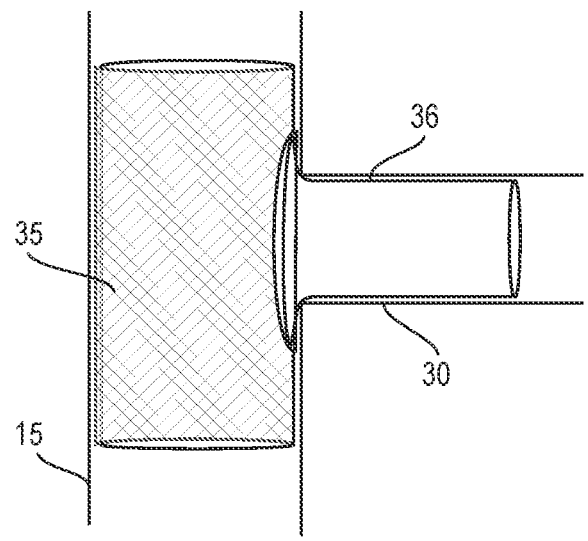
FIG. 16 is a schematic diagram illustrating a blood vessel with a main branch stent and a side branch stent in accordance with embodiments of the present disclosure.

Both the main branch and side branch balloons are deflated simultaneously. The balloon catheters are retracted one at a time over wire 90. Confirmatory angiogram is performed to evaluate for resolution of stenosis and to assess any associated complication. The guidewires are then removed to arrive at the structure of FIG. 16.

The disclosed stent assembly and method therefore provide an improved technique that can be used in the treatment of bifurcation lesions. The disclosed method advantageously maintains optimal side branch patency, thus reducing the rate of restenosis (e.g., the recurrence of abnormal narrowing of an artery after corrective surgery).

Further, the disclosed method prevents obstruction of the side branch that can occur due to plaque shifting during intervention. In this way, the rates of loss of the side branch are reduced compared to prior art methods.

As described above, the disclosed method achieves minimal strut overlap between the main branch and the side branch stents. In this way, deformation of the main branch stent is prevented. Thus, the disclosed method reduces the interference of strut and allows for adequate dilation of the side branch ostium by modifying the proximal edge of the stent in the side branch to conform to the lateral wall of the main branch and aligning it with the opening (e.g., orifice/aperture) of the main branch stent.

Continuing, the disclosed method advantageously provides reinforcement to the arterial wall at the ostium of the side branch without having the stent extend into the parental (main) vessel lumen. It also provides an unobstructed conduit for future interventions in the side branch when necessary.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Construction of Stent Models

Four stent models were constructed using Fibatape® self-adhesive fiberglass mesh tape (available from Saint-Gobain Adfors, La Defense, Courbevoie, France) as follows:

Stent 1: 1.25 inch diameter (provisional stent) with a length of 2 inches.

Stent 2: 0.75 inch diameter (side branch stent) with a length of 2 inches.

Stent 3: 1.25 inch diameter and a length of 2 inches with 0.75 inch diameter central orifice created in the middle of the longitudinal axis using scissors and orthodontic pliers.

Stent 4: 0.75 inch diameter with a length of 2 inches and provision for creating a proximal flare (modified technique stent). The provision for flaring was achieved by cutting into the proximal end of side branch stent into 5 segments each of the 4 mm length using scissors.

Example 2

Construction of Bifurcation Model

A tub was filled with 110 gallons of tap water at 55.4° F. A Lifegard Aquatics Quiet One® Pro Model 4000 pump (available from Lifegard Aquatics, Cerritos, California) was used to pump water into the model at a rate of 1022 gph (gallons per hour). One end of a polycarbonate tube with an inner diameter of 36 millimeters (mm) and length of 36 inches was connected to a 1×1×0.75 inch chlorinated polyvinyl chloride (CPVC) T-joint. The other end of the tube was connected to the pump. A second polycarbonate tube with inner diameter of 36 mm and length of 12 inches was attached to the second end of the T-joint. A polycarbonate tube with inner diameter 16.5 mm and length of 2 inches was attached to the middle opening of the T-joint.

A venturimeter to measure the rate of flow through the tube was constructed by creating a constriction in the 16.5 mm inner diameter tube using a pipe with inner diameter 12 mm and 2 CPVC couplers. Rubber o-rings were used to ensure a watertight seal. A drill was used to create 2 holes (e.g., 1 in the 16.5 mm tube and 1 in the 12 mm tube). Each hole measured 8 mm. Two ballpen barrels with a length of 4.7 inches and a diameter of 8 mm were used as piezometers.

Modeling clay with a thickness of 0.3 inches was used to simulate a plaque with length 12 mm located at the junction of the smallest diameter of the T-joint and the 16.5 mm inner diameter polycarbonate tube. The outer diameter of the simulated lesion was 16.5 mm and the inner diameter was about 8 mm to simulate 50% lesion. A flange of 3 mm was created as part of the lesion in the main branch.

The model was placed on a box to achieve elevation of 7 inches and was stabilized using a cord to minimize movement that could produce inaccurate results.

Example 3

Testing of Stent Models in Bifurcation System

Control: the bifurcation lesion was located at the side branch ostium with no stent. The pump was initiated, initial calibration was performed, and air bubbles were eliminated by gentle tapping. Measurements of water levels in piezometers 1 and 2 were taken using a 12-inch standard ruler from the reference points to the lower meniscus. A timer was used to allow 30 seconds before each reading to ensure the water levels remained constant. Ten trials were performed for the setup involving lesion with no stent. Measurements were taken twice for each trial to ensure accuracy.

Stent 1 (provisional stent): The stent was constricted and carefully placed in the middle of the 1 inch inner diameter of the T-joint using tweezers and a flashlight. The stent was expanded to approximate the inner diameter of the pipe. Water levels in both piezometers were recorded. Stent 1 was then removed.

The experiment was repeated for Stents 2-4.

Ten trials were conducted and piezometer readings were recorded.

The pressure difference between the two sections were observed as the difference in water in the piezometers attached to both sections, used to calculate the rate flow of the fluid flowing through the pipe.

TABLE 1

| | | Flow Rate | | |
|---|---|---|---|---|
| | | Stent | | |
| Trial # | T-Stent | Provisional Stent | Control (No Stent) | Modified Dual Stent |
| 1 | 1.67E−04 | 1.48E−04 | 1.64E−04 | 1.76E−04 |
| 2 | 1.67E−04 | 1.47E−04 | 1.65E−04 | 1.74E−04 |
| 3 | 1.68E−04 | 1.44E−04 | 1.67E−04 | 1.76E−04 |
| 4 | 1.65E−04 | 1.48E−04 | 1.63E−04 | 1.77E−04 |
| 5 | 1.68E−04 | 1.47E−04 | 1.64E−04 | 1.76E−04 |
| 6 | 1.67E−04 | 1.44E−04 | 1.65E−04 | 1.76E−04 |
| 7 | 1.65E−04 | 1.50E−04 | 1.65E−04 | 1.74E−04 |
| 8 | 1.69E−04 | 1.45E−04 | 1.65E−04 | 1.76E−04 |
| 9 | 1.68E−04 | 1.50E−04 | 1.64E−04 | 1.76E−04 |
| 10 | 1.69E−04 | 1.45E−04 | 1.67E−04 | 1.77E−04 |

Figure 17:
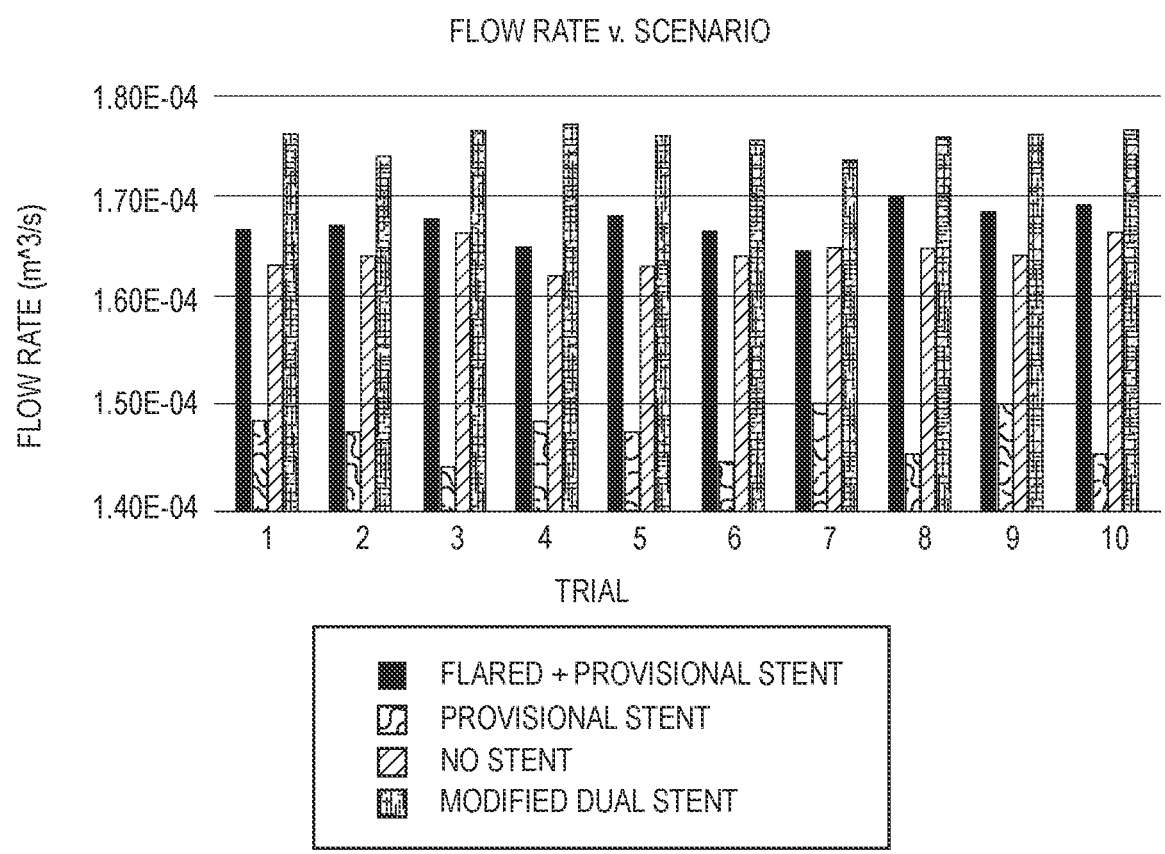
FIG. 17 is a bar graph illustrating flow rate versus trial for each of four scenarios of a first example.
Figure 18:
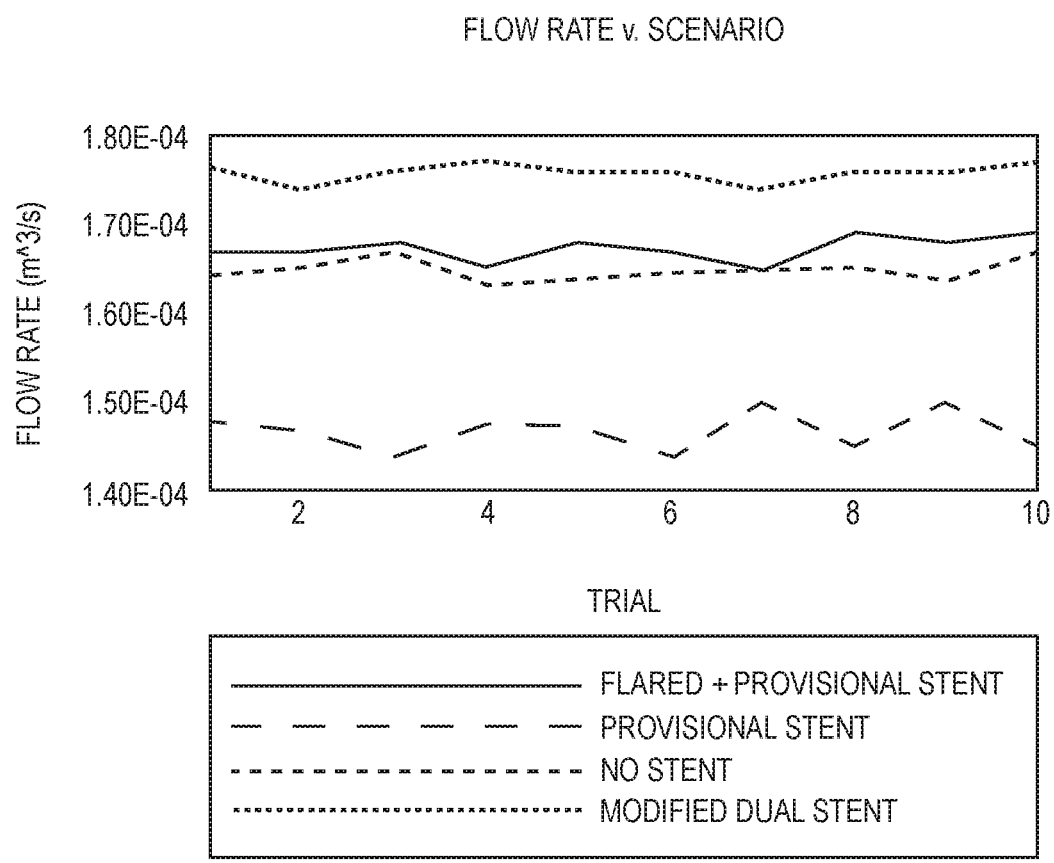
FIG. 18 is a graph depicting flow rate versus trial for each of the four scenarios of the first example.

FIGS. 17 and 18 illustrate graphs of the flow rate ($m^3/s$) of the flared+provisional stent, provisional stent, control (no stent), and modified dual stent for each of the 10 trials. As shown, the flow rate for the modified dual stent was the greatest.

The fluid flow rate through the side branch was lowest using the provisional stent, which can be attributed to the jailing of the side branch by the struts of the main branch stent, and to the side branch lesion not being treated, which caused flow interferences.

The flow rate of the modified dual stents was the highest compared to the control (20% higher), provisional, and T-stents, which support the finding that the fluid volume flow rate through the side branch of a bifurcation will be higher using the modified dual stent technique compared to the provisional and T-stent techniques.

Further, statistical analysis of the results revealed a p-value of 0.0029. Since $p<0.05$, there is a statistically significant difference between the flow rates in each scenario.

What is claimed is:

1. A method of deploying a dual stent assembly at a lesion site located at a bifurcation site in a vessel defined by a main branch and a side branch, the method comprising:
    positioning a side branch stent in the side branch of the bifurcation site, wherein the side branch stent comprises a body and a proximal flare configured at a proximal end, and wherein the side branch stent is positioned such that the proximal end is aligned with an ostium of the vessel;
    deploying the side branch stent in close approximation to a side branch vessel wall;
    performing balloon angioplasty within the main branch to crimp the proximal end of the side branch stent against the main branch walls; and
    after performing balloon angioplasty, positioning a main branch stent in the main branch of the bifurcation site, wherein the main branch stent comprises a main body with a longitudinal axis and a central orifice in a central portion of the longitudinal axis, and wherein the central orifice is aligned with the proximal flare of the side branch stent upon expansion of the main branch stent from a compressed orientation to a radially expanded orientation,
    wherein the dual stent assembly is deployed at a lesion site located at the bifurcation site.

2. A method of deploying a dual stent assembly at a lesion site located at a bifurcation site in a vessel defined by a main branch and a side branch, the method comprising:
    predilating the side branch and the main branch of the vessel by positioning a main branch balloon catheter in the main branch and a side branch balloon catheter in the side branch of the bifurcation site, and then dilating the main branch balloon catheter and the side branch balloon catheter using an inflation device;
    deflating the main and side branch balloon catheters;
    retracting the main and side branch balloon catheters from the bifurcation site;
    positioning a side branch stent in the side branch of the bifurcation site, wherein the side branch stent comprises a body and a proximal flare configured at a proximal end, and wherein the side branch stent is positioned such that the proximal end is aligned with an ostium of the vessel;
    positioning the main branch balloon catheter in the main branch of the bifurcation site; simultaneously deploying the side branch stent in close approximation to a side branch vessel wall at a first pressure using a side branch stent balloon and inflating the main branch balloon catheter at a second pressure, wherein the first pressure is greater than the second pressure, whereby the proximal flare is opened;
    deflating the side branch stent balloon and the main branch balloon catheter;
    crimping the proximal end of the side branch stent by inflating the main branch balloon catheter to a pressure that is greater than the second pressure;
    deflating and retracting the main branch balloon catheter;
    retracting a side branch guide wire to a proximal portion of the main branch;
    positioning a main branch stent in the main branch of the bifurcation site, wherein the main branch stent comprises a main body with a longitudinal axis and a central orifice in a central portion of the longitudinal axis, and wherein the central orifice is aligned with the proximal flare of the side branch stent;
    inflating a main branch stent balloon to a third pressure greater than the second pressure;
    removing the main branch stent balloon;
    rewiring the side branch using a guide wire;
    positioning the main branch balloon catheter in the main branch of the bifurcation site and the side branch balloon catheter in the side branch of the bifurcation site;
    performing simultaneous kissing inflation of the main branch balloon catheter and the side branch balloon catheter; and
    simultaneously deflating and retracting the main branch balloon catheter and the side branch balloon catheters, wherein the dual stent assembly is deployed at a lesion site located at the bifurcation site.

3. The method of claim 2, wherein the main branch stent, side branch stent, or both are constructed from one or more biocompatible materials.

4. The method of claim 3, wherein the one or more biocompatible materials include a metal selected from stainless steel, nitinol, cobalt, cobalt-based alloy, gold, tantalum, platinum, platinum iridium, niobium, tungsten, nickel, titanium, stainless steel/titanium composite, chromium, cobalt/chromium alloys, magnesium, aluminum, or combinations thereof.

5. The method of claim 3, wherein the one or more biocompatible materials include a polymeric material selected from cellulose acetate, cellulose nitrate, silicone, polyethylene terephthalate, polyurethane, polyamide, polyester, polyorthoester, polyanhydride, polyether sulfone, polycarbonate, polypropylene, ultra-high molecular weight polyethylene, polytetrafluoroethylene, polylactic acid, polyglycolic acid, polyanhydride, polycaprolactone, polyhydroxybutyrate valerate, or combinations thereof.

6. The method of claim 2, wherein the central orifice is configured in a round, hexagonal, octagonal, or oval shape.

7. The method of claim 2, wherein the central orifice has a diameter of about 2 to 20 mm.

8. The method of claim 2, wherein the mam branch stent, side branch stent, or both comprise one or more radiopaque materials selected from bismuth (and salts thereof), barium (and salts thereof), tantalum, tungsten, halfnium, gold, platinum, molybdenum, zirconium oxide, titanium, and combinations thereof.

9. The method of claim 2, wherein the mam branch stent, side branch stent, or both comprises one or more therapeutic agents selected from antineoplastic agents, antiproliferative agents, antibiotics, antithrombogenic agents, anticoagulants, antiplatelet agents, anti-inflammatory agents, or combinations thereof.

10. The method of claim 2, further comprising performing an angiogram to confirm proper positioning of the main branch stent, side branch stent, or both.

11. The method of claim 2, wherein the vessel is a coronary vessel.

* * * * *